United States Patent
Yamamoto et al.

(10) Patent No.: US 6,214,612 B1
(45) Date of Patent: *Apr. 10, 2001

(54) CHOLESTEROL SENSOR CONTAINING ELECTRODES, CHOLESTEROL DEHYDROGENASE, NICOTINAMIDE ADENINE DINUCLEOTIDE AND OXIDIZED ELECTRON MEDIATOR

(75) Inventors: Tomohiro Yamamoto, Neyagawa; Shin Ikeda, Katano; Toshihiko Yoshioka; Shiro Nankai, both of Hirakata; Junko Iwata, Onsen-gun, all of (JP)

(73) Assignee: Matsushita Electric Industrial Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/806,801

(22) Filed: Mar. 3, 1997

(30) Foreign Application Priority Data

Mar. 7, 1996 (JP) ...................................... 8-049933

(51) Int. Cl.$^7$ .............................. C12M 1/34; C12Q 1/60; C12Q 1/32; G01N 27/26
(52) U.S. Cl. ......................... 435/287.1; 204/403; 435/11; 435/26; 435/287.3; 435/817
(58) Field of Search ................. 435/11, 25, 26, 435/287.1, 287.3, 817; 204/403

(56) References Cited

U.S. PATENT DOCUMENTS

| | | | |
|---|---|---|---|
| 4,040,908 | 8/1977 | Clark, Jr. ........................ | 195/103.5 |
| 5,322,680 | * 6/1994 | Beck et al. ...................... | 428/71 |
| 5,650,062 | * 7/1997 | Ikeda et al. ..................... | 205/778 |
| 5,658,443 | * 8/1997 | Yamamoto et al. ............... | 204/403 |

FOREIGN PATENT DOCUMENTS

| | | |
|---|---|---|
| 0 125 867 A2 | 11/1984 | (EP) . |
| 0 177 743 A2 | 4/1986 | (EP) . |
| 0 230 786 A1 | 8/1987 | (EP) . |
| 3-201998 | 9/1991 | (JP) . |
| WO89/08713 | 9/1989 | (WO) . |

* cited by examiner

Primary Examiner—David M. Naff
(74) Attorney, Agent, or Firm—Akin, Gump, Strauss, Hauer & Feld, L.L.P.

(57) ABSTRACT

A cholesterol sensor for quantitative determination of cholesterol is provided containing an electrode system and a reaction reagent system. The electrode system contains a measuring electrode such as a carbon electrode and a counter electrode, and the reaction reagent system contains cholesterol dehydrogenase, nicotinamide adenine dinucleotide and an oxidized electron mediator. Electron mediators include ferricyanide, 1,2-naphthoquinone-4-sulfonate, 2,6-dichlorophenol indophenol, dimethylbenzoquinone, 1-methoxy-5-methylphenazinium sulfate, methylene blue, gallocyanine, thionine, phenazine methosulfate and Meldola's blue. Diaphorase, cholesterol esterase and a surfactant may also be present. The electrode system is on an insulating base plate, and the base plate has a covering member containing a groove that is a sample supplying channel which extends from an end of the base plate to the electrode system. A reaction layer containing the reagent system in dry form and a layer of a hydrophilic polymer is provided on the base plate or the covering member, or on both the electrode system and covering member so as to be exposed to the sample supplying channel. During operation, the electron mediator is reduced in conjunction with oxidation of cholesterol in a sample by cholesterol dehydrogenase, and an amount of current required to electrochemically re-oxidize the electron mediator is directly proportional to a quantity of cholesterol present in the sample.

9 Claims, 8 Drawing Sheets

CHOLESTEROL SENSOR CONTAINING ELECTRODES, CHOLESTEROL DEHYDROGENASE, NICOTINAMIDE ADENINE DINUCLEOTIDE AND OXIDIZED ELECTRON MEDIATOR

BACKGROUND OF THE INVENTION

The present invention relates to a cholesterol sensor capable of performing quantitative determination of cholesterol in a sample with high accuracy in a rapid and simplified manner.

As a system for quantitatively determining a specific component in a sample without requiring dilution or stirring of the sample solution in a rapid and simplified manner, various types of biosensors have heretofore been proposed.

First, a glucose sensor will be described as an example of the biosensors.

As a method for quantitative determination of glucose which utilizes an enzyme electrode, generally known is a system comprising a combination of glucose oxidase and an oxygen electrode or a hydrogen peroxide electrode. The glucose oxidase selectively oxidizes a substrate i.e., β-D-glucose to D-glucono-δ-lactone by utilizing oxygen as an electron mediator. By this reaction, oxygen is reduced to hydrogen peroxide. Quantitative determination of glucose is performed by measuring the amount of oxygen consumed by the oxygen electrode in this reaction, or by measuring the amount of hydrogen peroxide produced in this reaction by the hydrogen peroxide electrode of a platinum electrode or the like.

By the above-mentioned method, however, it is impossible to measure glucose concentrations under a condition lacking oxygen. This is why a glucose sensor which does not utilize oxygen but utilizes a metal complex such as potassium ferricyanide, a ferrocene derivative, a quinone derivative or the like, or another organic compound as the electron mediator has been developed. In this type of glucose sensor, reductant of electron mediator produced by enzyme reaction is oxidized by an electrode, and the concentration of glucose is determined by measuring the current required for this oxidation. This mode of measurement has been widely applied to quantitative determination of substrates other than glucose.

As an example of this type of biosensor, a glucose sensor which will be subsequently described is known (Japanese Laid-Open Patent Publication Hei 2-062952).

That is, the disclosed glucose sensor comprises an electrode system of a measuring electrode, a counter electrode and a reference electrode provided on an insulating base plate by means of screen printing or the like, and a reaction layer including a reaction reagent system of a hydrophilic polymer, an oxidoreductase, and an electron mediator, and, if required, a buffer agent is added thereto.

When a sample solution containing a substrate is dropped on the reaction layer, the reaction layer is dissolved and adjusted to a pH value where the highest enzyme activity is obtainable by a buffer action of the buffer agent, the enzyme is allowed to react with the substrate, and the electron mediator is reduced. After completion of the enzyme reaction, the reduced electron mediator is oxidized electrochemically, and the substrate concentration of the sample solution is derived from a current required for the oxidation.

Measurements on various substances are theoretically possible with the biosensors of this type, by using a particular enzyme which has a substrate specificity to the substance to be measured.

When cholesterol oxidase is employed as the oxidoreductase, it is possible to configure a biosensor for measuring cholesterol in serum. Serum cholesterol level used as an index for diagnosis is however a sum of the concentrations of cholesterol and cholesterol ester in serum. Since the cholesterol ester cannot act as the substrate for the oxidation reaction by the cholesterol oxidase, it is required to combine a process of converting the cholesterol ester into cholesterol in order to determine the serum cholesterol level as the index for the diagnosis. This is because the currently employed method is performed on the basis of the following general reaction scheme:

Cholesterol ester+$H_2O$→Cholesterol+Fatty acid
Cholesterol+Electron mediator (oxidized form)
→Cholestenone+Electron mediator (reduced form)
Electron mediator (reduced form)→Electron mediator (oxidized form)

However, if a compound other than oxygen is used as the electron mediator to cause oxidation reaction of cholesterol by the cholesterol oxidase as described above, the rate of secondary reaction between the oxygen and the enzyme becomes faster than the rate of secondary reaction between the electron mediator and the enzyme. This causes a tendency that in the case of dissolution of oxygen in the sample solution, the oxidation current value of the electron mediator measured by the electrode becomes lower than the value estimated to be obtainable by the oxidation reaction of the substrate contained in a sample solution in complete conjugation with the reducing reaction of the electron mediator. The above-mentioned scheme therefore has a problem of inaccurate responses of the sensor particularly to the substrates of low concentrations in the sample solution. Another problem is prolonged reaction time, which poses further problems that an increase in the supported amount of cholesterol oxidase on the sensor in order to avoid time-consuming reaction leads to an increase in manufacturing cost, and that an increase in the supported amount of reagent on the sensor interferes with the fabrication of sensor physically.

BRIEF SUMMARY OF THE INVENTION

The object of the present invention is to provide a cholesterol sensor capable of performing rapid quantitative determination of cholesterol with high accuracy.

The present invention provides a cholesterol sensor comprising an electrode system including a measuring electrode and a counter electrode, and a reaction reagent system, wherein the reaction reagent system contains at least cholesterol dehydrogenase, nicotinamide adenine dinucleotide and an electron mediator.

It is preferable that the above-mentioned reaction reagent system contains cholesterol esterase and a surfactant.

In accordance with the present invention, it is possible to obtain a biosensor capable of rapidly measuring the cholesterol concentration without any influence by oxygen.

While the novel features of the present invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
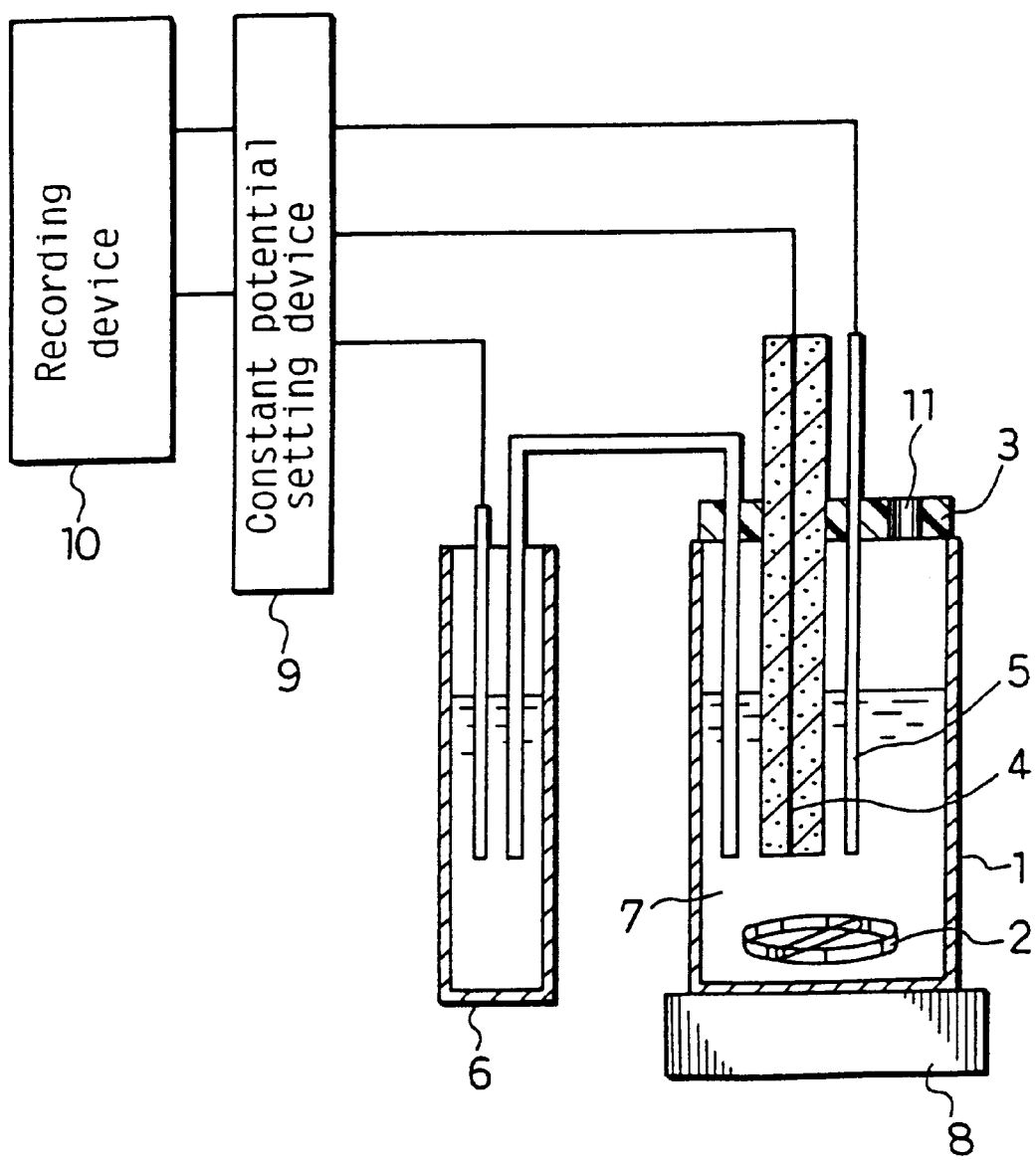
FIG. 1 is a schematic view showing the configuration of a cholesterol sensor in an embodiment of the present invention.

The cholesterol sensor in one mode of the present invention comprises a solution containing the above-mentioned reaction reagents and the electrode system immersed in the solution.

In another mode of the present invention, the reaction reagents are positioned in their dried states on or near the electrode system. This configuration provides a cholesterol sensor with a low manufacturing cost for measuring cholesterol in a simple and rapid way. That is, the main body of cholesterol sensor is constituted with an insulating base plate, an electrode system including a measuring electrode and a counter electrode which are provided on the above-mentioned insulating base plate, and a covering member having a groove which is placed on the above-mentioned insulating base plate for defining a sample supplying channel. The sample supplying channel is extended from an end of the base plate to the electrode system. And, a reaction layer including a reaction reagent system is provided on a part of the base plate or the covering member that is exposed to the sample supplying channel.

With respect to the cholesterol sensor of the above-mentioned configuration, several preferred modes relating to the positioning of the reaction layer will be described in the following paragraphs.

In a first mode of configuration, the reaction layer is positioned over the electrode system on the base plate. When the reaction layer is formed, it is preferable to form a layer of a hydrophilic polymer such as carboxymethyl cellulose over the electrode system in order to prevent the components of the reaction layer, enzyme and electron mediator from directly contacting the surface of the electrode system. This effectively inhibits an adverse change in the performance of the electrode system caused by adsorption of protein onto the surface of the electrode system and chemical action of a substance such as potassium ferricyanide having an oxidizing ability.

In a second embodiment of configuration, the reaction layer is divided into a plurality of layers to provide them over the electrode system on the base plate and the covering member. In the case that a reaction reagent includes as an electron mediator potassium 1,2-naphthoquinone-4-sulfonate which is relatively unstable at high pH and as a buffer agent tris (hydroxymethyl) aminomethane-hydrochloric acid buffer (hereinafter, abbreviated to "Tris hydrochloride") in particular, it is preferable to locate the electron mediator and the buffer agent separately. For instance, a layer of the electron mediator such as potassium 1,2-naphthoquinone-4-sulfonate is positioned on the part of the covering member which is exposed to the sample supplying channel and the reaction layer containing the buffer agent such as Tris hydrochloride is positioned over the electrode system on the base plate.

In a third embodiment of configuration, a layer of the electron mediator such as potassium 1,2-naphthoquinone-4-sulfonate and another layer containing the buffer agent such as Tris hydrochloride are positioned on the same base plate separately. For instance, the reaction layer including the above-mentioned buffer agent is formed over the electrode system, and the layer including the electron mediator such as potassium 1,2-naphthoquinone-4-sulfonate is provided on a part upstream to the electrode system, i.e, on a part proximal to the open inlet of the sample supplying channel. It is preferable to form a layer of the hydrophilic polymer beneath the latter layer, or to mix the hydrophilic polymer with the components of these layers.

A fourth embodiment of configuration has a layer of the hydrophilic polymer over the electrode system on the base plate, and a reaction layer is formed on a part of the covering member exposed to the sample supplying channel.

In the second and third embodiments of the configuration, it is also preferable to coat the electrode system with a layer of the hydrophilic polymer. In forming a layer including the electron mediator and the like on the covering member in the second and third embodiments of the configuration, it is also preferable to form a layer of the hydrophilic polymer beneath the electron mediator layer, or to mix the hydrophilic polymer with the components of the layer.

It is also preferable to provide a layer of lecithin on or near the above-mentioned reaction layer, for smooth introduction of the sample solution to the electrode system.

In the present invention, the preferable electron mediator is at least one member selected from the group consisting of a ferricyanide, 1,2-naphtoquinone-4-sulfonic acid, 2,6-dichlorophenol indophenol, dimethyl benzoquinone, 1-methoxy-5-methylphenazinium sulfate, methylene blue, gallocyanine, thionine, phenazine methosulfate and Meldola's blue.

It is also preferable to contain diaphorase in the reaction reagent system. The diaphorase catalyzes the reaction of the electron mediator with reductant of nicotinamide adenine dinucleotide and shortens the time period required for the measurement. In the case of employing the electron mediator such as potassium 1,2-naphthoquinone-4-sulfonate which causes very rapid oxidation-reduction reaction with the reductant of nicotinamide adenine dinucleotide without the aid of the catalytic action of diaphorase, the diaphorase is not particularly required.

In the following paragraphs, specific examples of the present invention will be described.

EXAMPLE 1

FIG. 1 schematically shows a cholesterol sensor in accordance with this example. A glass cell 1 which contains a stirrer piece 2 is fixed on a stirring machine 8. The glass cell 1 also contains a measuring electrode 4, a counter electrode 5 and a reference electrode 6 which are set to the glass cell by an electrode fixing device 3. The measuring electrode 4 is a glassy carbon electrode and the counter electrode 5 is a platinum electrode. The reference electrode 6 is a silver/silver chloride electrode and is connected to the glass cell through a salt bridge of agarose gel impregnated with potassium chloride (KCl) solution. These electrodes are respectively connected to a recording device 10 through a constant potential setting device 9. A measuring apparatus system of this specific example is configured with the above-mentioned components.

The above-mentioned glass cell 1 is filled with a reaction solution 7 which is stirred by the stirring piece 2. The reaction solution 7 is a buffer aqueous solution of Tris hydrochloride containing cholesterol dehydrogenase (hereinafter abbreviated to "ChDH"), nicotinamide adenine dinucleotide (hereinafter abbreviated to "NAD"), potassium ferricyanide as the electron mediator and diaphorase. The desirable concentrations of the respective reaction reagents are as follows:

ChDH:10 unit/ml, NAD:25 mM/l, diaphorase:20 unit/ml, potassium ferricyanide:100 mM/l, and Tris hydrochloride:0.3 M/l.

Apart from the above-exemplified desirable concentrations, it is possible to obtain an appropriate response by the use of partly different concentrations if required according to a different measuring condition. It is desirable to adjust the pH value of the reaction solution to 8.0 to 9.0. If the pH value is lower than 8.0, the time period required for the reaction is remarkably increased, and if the pH value is not less than 9.0, the current value per unit concentration of cholesterol is made small and conversely a residual current value, presumably due to chemical reaction other than the enzyme reaction, is increased.

A potential of 500 mV is applied to the above-mentioned measuring electrode 4 with respect to the reference electrode 6. When a sample solution containing cholesterol is dropped on the reaction solution 7 through a port 11 provided on the electrode fixing device 3, the cholesterol is oxidized to cholestenone by the ChDH. Conjugated with this reaction, the NAD is reduced to NADH. The produced NADH donates/accepts electrons to and from ferricyanide ions and is oxidized again to NAD. The ferricyanide ions receive electrons from the NADH and are reduced to ferrocyanide ions.

The concentration of the ferrocyanide ions produced in the above-mentioned manner is directly proportional to the cholesterol concentration of the sample solution. This oxidation/reduction reaction is catalyzed by the diaphorase. Although the reaction proceeds spontaneously under a condition lacking the diaphorase, it is possible to proceed the reaction very rapidly in the presence of diaphorase.

As described previously, since the potential of 500 mV is applied to the measuring electrode 4 with respect to the reference electrode 6, the ferrocyanide ions donate electrons to the measuring electrode 4 and return to ferricyanide ions. Further, since the measuring electrode 4 is a glassy carbon electrode and the potential of the solution in the vicinity of the measuring electrode 4 is 500 mV with respect to the silver/silver chloride electrode, it is believed that the amount of the NADH which is electrochemically oxidized at the measuring electrode is very small. By observing the transferring of the electrons accepted by the measuring electrode 4 as an electric current, it is possible to quantitatively determine the cholesterol concentration of the sample solution. In the case of serum wherein the sample solution contains cholesterol ester therein, it is possible to measure a sum of the concentrations of cholesterol ester and cholesterol by adding cholesterol esterase and a surfactant for promoting the catalytic property of the cholesterol esterase to the reaction solution 7 in addition to the above-mentioned components.

Figure 2:
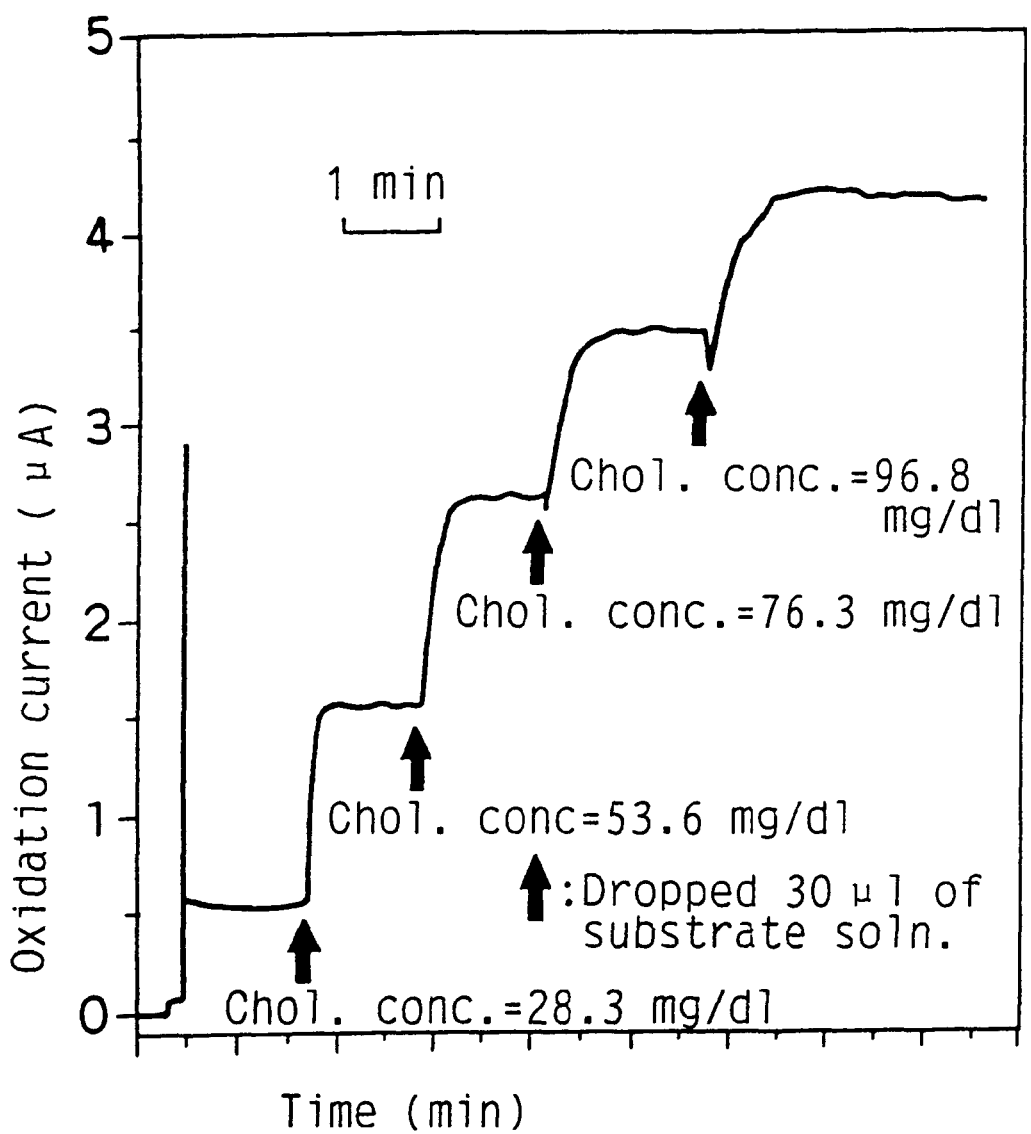
FIG. 2 is a diagram showing a measurement result obtained by the cholesterol sensor of the shown embodiment.
Figure 3:
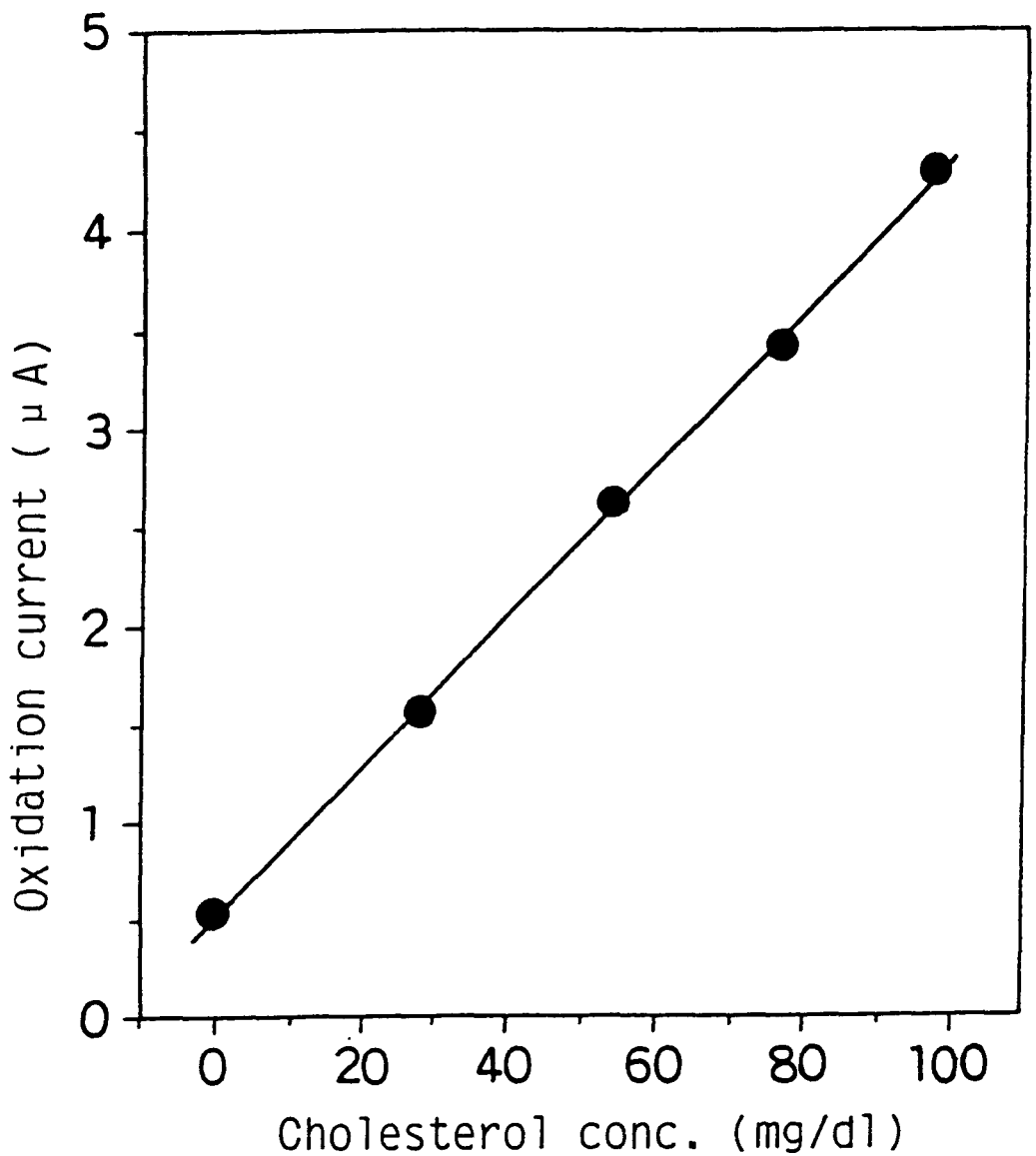
FIG. 3 is a diagram showing a relationship between the cholesterol concentration and the current value in an example of measurement result obtained with the cholesterol sensor of the shown embodiment.

FIG. 2 and FIG. 3 show the results of the measurements performed in accordance with this example.

FIG. 2 is a diagram showing a change in the current value. The respective arrows in the figure represent the respective cholesterol concentrations in the reaction solution after addition of drops of the substrate solution (30 $\mu$l) to the reaction solution. FIG. 3 is a diagram showing a relationship between the current value and the cholesterol concentration of FIG. 2. As shown by these diagrams, with the dropping of the cholesterol, the current value increases and reaches to a steady value in a minute or so and the current value shows a very preferable linear relationship with the cholesterol concentration.

EXAMPLE 2

Figure 4:
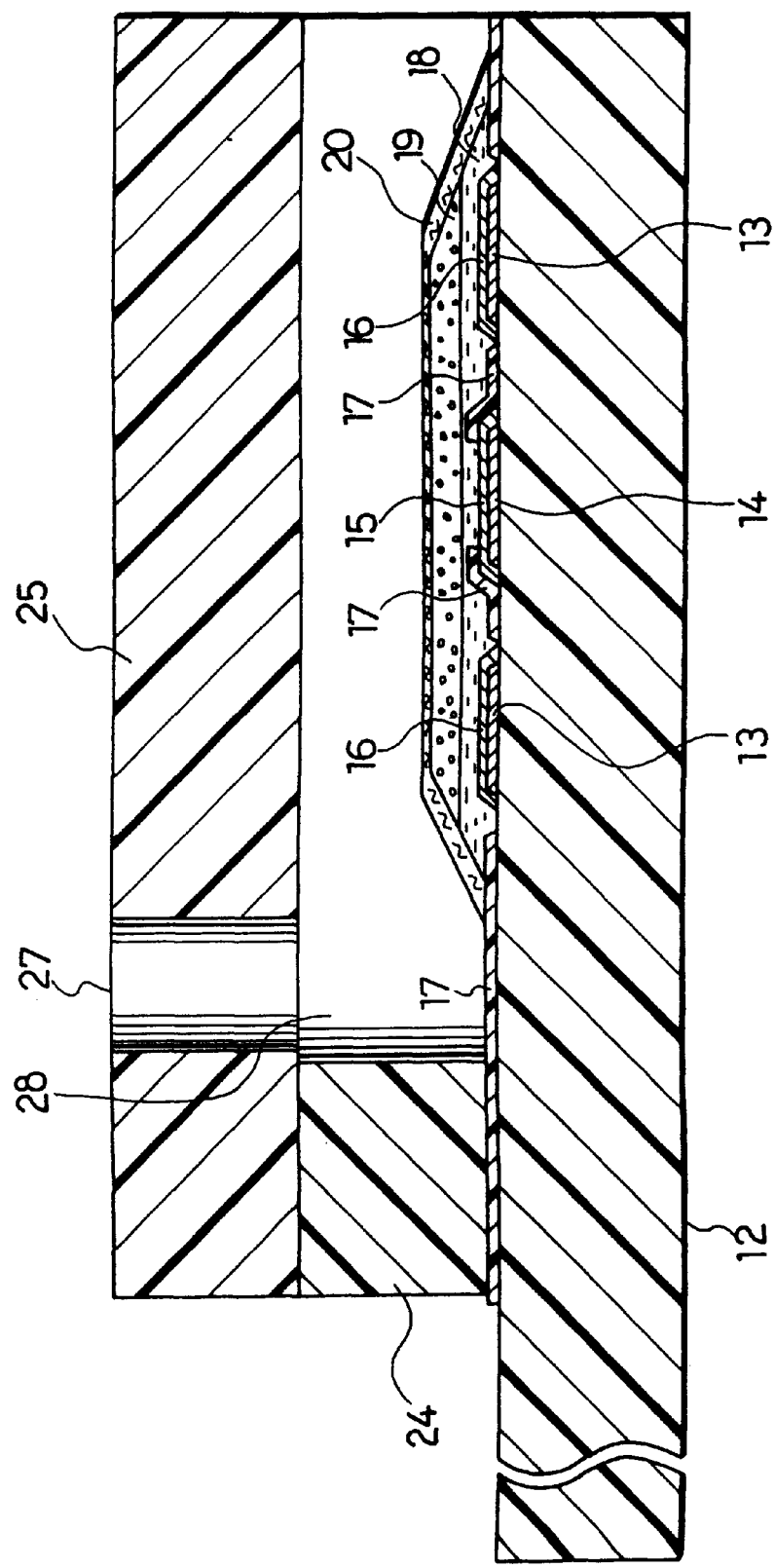
FIG. 4 is a longitudinal cross-sectional view showing the configuration of an essential part of the cholesterol sensor in another embodiment of the present invention.
Figure 5:
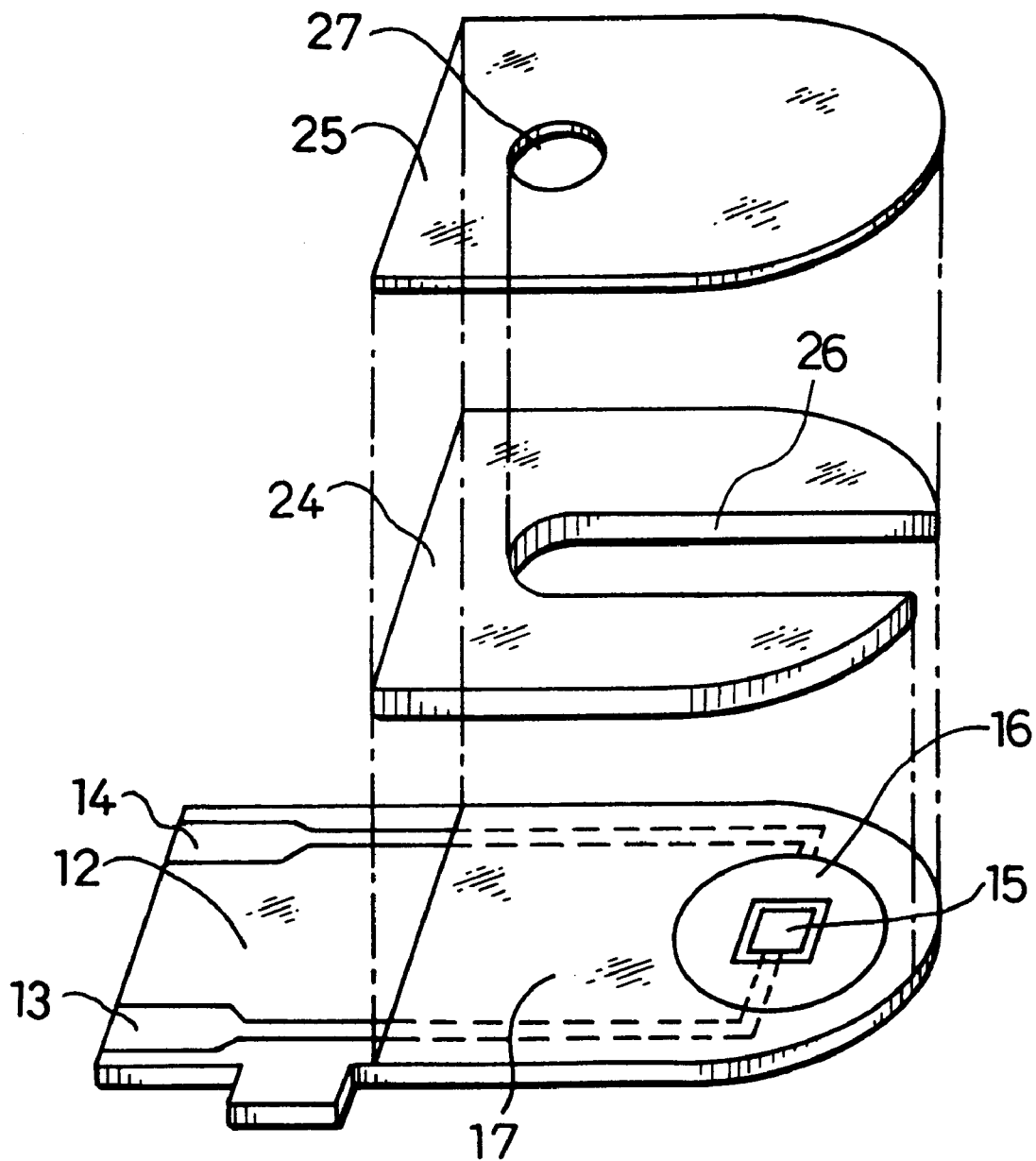
FIG. 5 is an exploded perspective view showing the disclosed cholesterol sensor with an omission of the reaction layer.

FIG. 4 is a longitudinal cross-sectional view showing the cholesterol sensor in accordance with this example, and FIG. 5 is an exploded perspective view of the cholesterol sensor with an omission of the reaction layer.

In these figures, an insulating base plate 12 is made of polyethylene terephthalate. On this insulating base plate 12, lead conductors 13 and 14 of silver paste are formed by means of screen printing. An electrode system including a measuring electrode 15 and a counter electrode 16 is formed by printing an electrically-conductive carbon paste containing a resin binder, and an insulating layer 17 on this insulating base plate 12 by printing an electrically insulating paste, respectively. The insulating layer 17 serves to define areas of the exposed parts of the measuring electrode 15 and the counter electrode 16 to be constant and to partly cover the lead conductors 13 and 14.

After the part of the electrodes is configured in this manner, an aqueous solution of a hydrophilic polymer, sodium salt of carboxymethyl cellulose (hereinafter abbreviated to "CMC") (0.5 wt %) is dropped on the electrode system and dried in a hot dryer at 50° C. for 10 minutes, thereby to form a CMC layer 18.

Then, prepared is a mixed aqueous solution containing ChDH derived from Nocardia species in 10 unit/ml, NDA which is a co-enzyme in 50 mM/l, diaphorase which is an enzyme derived from Pseudomonas species in 10 unit/ml, potassium ferricyanide which is an electron mediator in 50 mM/l, cholesterol esterase (hereinafter abbreviated to "ChE") derived from Pseudomonas species in 1 k unit/ml, n-octyl-$\beta$-D-thioglucoside which is a surfactant in 0.5 wt %, and Tris hydrochloride which is a buffer agent in 0.3 M/l, and the mixture is adjusted to pH 8.5.

By dropping this mixed aqueous solution (5 $\mu$l) on the CMC layer 18 and drying it in an air dryer at room temperature for 30 minutes, a ChDH-ChE-potassium ferricyanide-surfactant-NAD-diaphorase-buffer agent layer 19 is formed.

In this layer, CMC is partly mixed with ChDH, ChE, potassium ferricyanide, n-octyl-$\beta$-D-thioglucoside, NAD, and a buffer agent, and the whole is in a state of a thin film having a thickness of several microns. That is, when the above-mentioned mixed aqueous solution is dropped on the CMC layer, the firstly formed CMC layer is once dissolved and in the subsequent drying process, a layer is formed again in a state of being mixed with the enzyme etc. However, since this process does not use stirring or the like, a completely mixed state is not brought about and a state of the surface of the electrode system covered only with CMC is maintained. By virtue of this process, the enzyme, the electron mediator and the like are not in contact with the surface of the electrode system, whereby a change in the characteristics of the electrode system due to the adsorption of protein onto the surface of the electrode system or chemical action by the substance having an oxidizing ability such as potassium ferricyanide becomes less likely to occur. As a result, it is possible to obtain a sensor having a sensor response with high accuracy.

On this ChDH-ChE-potassium ferricyanide-surfactant-NAD-diaphorase-buffer agent layer 19, 5 µl of a 0.5 wt % toluene solution of phosphatidyl choline is dropped and dried, thereby to form a lecithin layer 20. This lecithin layer facilitates smooth introduction of the sample solution. This lecithin layer is not indispensable for the enzyme reaction.

After forming the reaction layer comprising the CMC layer 18, the ChDH-ChE-potassium ferricyanide-surfactant-NAD-diaphorase-buffer agent layer 19, and the lecithin layer 20, the cholesterol sensor is completed by adhering a covering member composed of a spacer 24 and a cover 25 to the insulating base plate 12 in a positional relationship as indicated by the one dot-chain lines in FIG. 4. In the sensor assembled in this manner, a sample supplying channel 28 (shown in FIG. 4) is formed by a slit 26 of the spacer 24, as shown in FIG. 5.

This cholesterol sensor easily introduces the sample solution into a part of the reaction layer, simply bringing the sample solution in contact with an open inlet part of the sample supplying channel 28 at the tip of the sensor. Since the supplying amount of the sample solution depends on a volume of the sample supplying channel 28, it is not necessary to previously quantifying the amount. It is further possible to suppress evaporation of the sample solution during the measurement, thereby to enable a measurement with high accuracy. In FIG. 4, numeral 27 designates an air vent provided on the cover 25. When a transparent polymer is used as the material for the cover 25 and the spacer 24, it is easily possible to observe the state of the reaction layer and the condition of introducing the sample solution from outside the sensor.

Three minutes after a supply of the sample solution of 3 µl of a cholesterol standard solution to the thus configured cholesterol sensor through the open inlet of the sample supplying channel 28, a pulse voltage of +0.5 V is applied to the measuring electrode in an anodic direction, using the counter electrode as a reference, and the current value after 5 seconds is measured.

When the sample solution reaches the reaction layer, the solution first dissolves the lecithin layer 20, and subsequently dissolves the ChDH-ChE-potassium ferricyanide-surfactant-NAD-diaphorase-buffer agent layer 19. The cholesterol ester contained in the sample solution is dispersed again by n-octyl-β-D-thioglucoside contained in the ChDH-ChE-potassium ferricyanide-surfactant-NAD-diaphorase-buffer agent layer 19, and then converted into cholesterol by the catalytic action of the ChE. The produced cholesterol is oxidized by the ChDH, and the NAD is reduced in conjugation with the oxidation reaction, thereby to produce NADH. Further, the produced NADH is oxidized again by the catalytic action of the diaphorase to return to the NAD. In conjugation with the oxidation reaction of the NADH, the ferricyanide ions are reduced to ferrocyanide ions.

Application of the above-mentioned pulse voltage generates an oxidation current for both the produced ferricyanide ions and partial NADH. The current value corresponds to the concentration of the substrate cholesterol.

In this process, although there is a possibility that the observed current value includes the oxidation current for partial NADH, it is believed that a current attributed to an electrochemical oxidation of the NADH on the measuring electrode occupies a very small proportion of the whole measurement value, because the time period required for the measurement is shortened by the addition of the diaphorase to the reaction reagent system.

EXAMPLE 3

Figure 6:
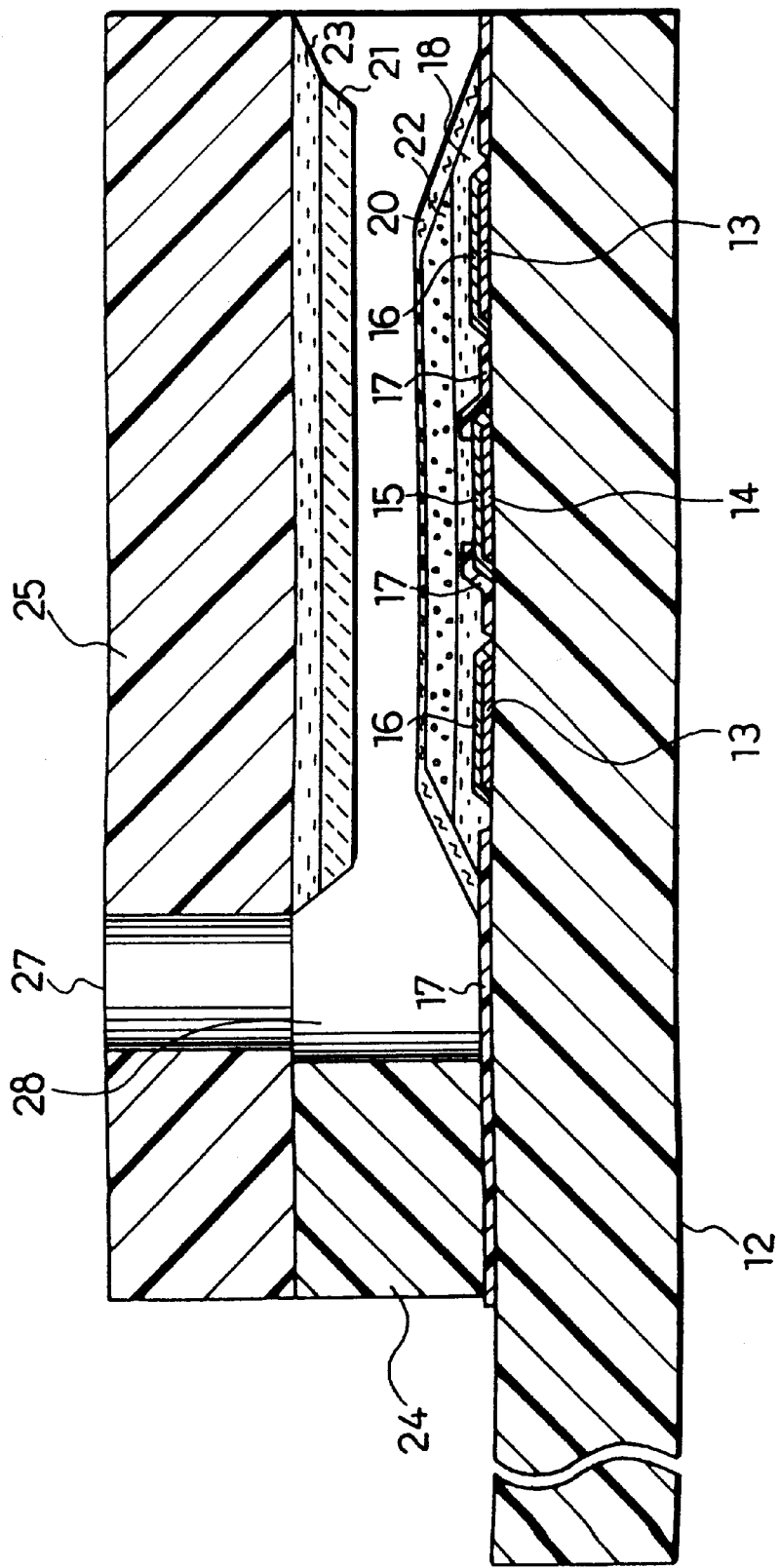
FIG. 6 is a longitudinal cross-sectional view showing the configuration of an essential part of the cholesterol sensor in still another embodiment of the present invention.

FIG. 6 is a longitudinal cross-sectional view of the cholesterol sensor of this example. The same reference numerals in FIG. 4 and FIG. 5 are used in the figure to designate the same or similar components, and this manner of designation will be applied to the subsequent description and drawings.

The CMC layer 18 is formed on the electrode system of the base plate in a manner similar to that in Example 2. On a recessed part of the covering member configured with the spacer 24 and the cover 25 corresponding to the slit 26 of the spacer 24 exposed to the sample supplying channel 28, another CMC layer 23 is formed by dropping a 0.5 wt % aqueous solution of CMC and subsequent drying. By dropping 5 µl of a 50 mM solution of potassium 1,2-naphthoquinone-4-sulfonate (hereinafter abbreviated to "NQS") so as to cover the CMC layer 23 and subsequent drying in air at room temperature, an NQS layer 21 is formed.

If a top-reaction layer is formed on the inner side of the covering member comprising the spacer 24 and the cover 25, it is preferable to provide this CMC layer 23, because the reaction layer becomes liable to fall off if the CMC layer 23 is omitted. Instead of the CMC layer 23 and the NQS layer 21, it is possible to provide a layer containing both CMC and NQS by dropping a CMC aqueous solution dissolving NQS.

Since NQS is relatively unstable at high pH, it should not be dissolved in a solution containing a buffer agent such as Tris hydrochloride and stood still for a long period after dissolution. However, if NQS is separated from the buffer agent as disclosed, it is possible to incorporate NQS into a sensor as the electron mediator.

Then, prepared is a mixed aqueous solution containing the ChDH derived from Nocardia species in 10 unit/ml, the NDA which is a co-enzyme in 50 mM/l, ChE derived from Pseudomonas species in 1 k unit/ml, n-octyl-β-D-thioglucoside which is the surfactant in 0.5 wt %, and Tris hydrochloride which is a buffer agent in 0.3 M/l, and the mixture is adjusted to pH 8.5.

By dropping this mixed aqueous solution (5 µl) over the CMC layer 18 on the electrode system and drying it in a dried air at room temperature for 30 minutes, a ChDH-ChE-surfactant-NAD-buffer agent layer 22 is formed.

In the case that NQS is used as the electron mediator which causes very rapid oxidation-reduction reaction with the NADH without the aid of the catalytic action of diaphorase, the diaphorase can be omitted as in this example. If it is necessary to shorten the measuring time further, the diaphorase may be included in the system of this example.

Over the ChDH-ChE-surfactant-NAD-buffer agent layer 22, a lecithin layer 20 is formed by dropping 5 µl of a 0.5 wt % toluene solution of phosphatidyl choline and subsequent drying in a manner similar to that of Example 2. In the above-mentioned manner, a bottom reaction layer of the cholesterol sensor is formed.

By combining the covering member comprising the spacer 24 and the cover 25 having the top reaction layer and the insulating base plate having the bottom reaction layer, a cholesterol sensor is completed. FIG. 6 shows the structure of the cholesterol sensor thus obtained.

The response for the cholesterol standard solution obtained with the cholesterol sensor thus configured shows an acceptable linearity to the cholesterol concentration.

EXAMPLE 4

Figure 7:
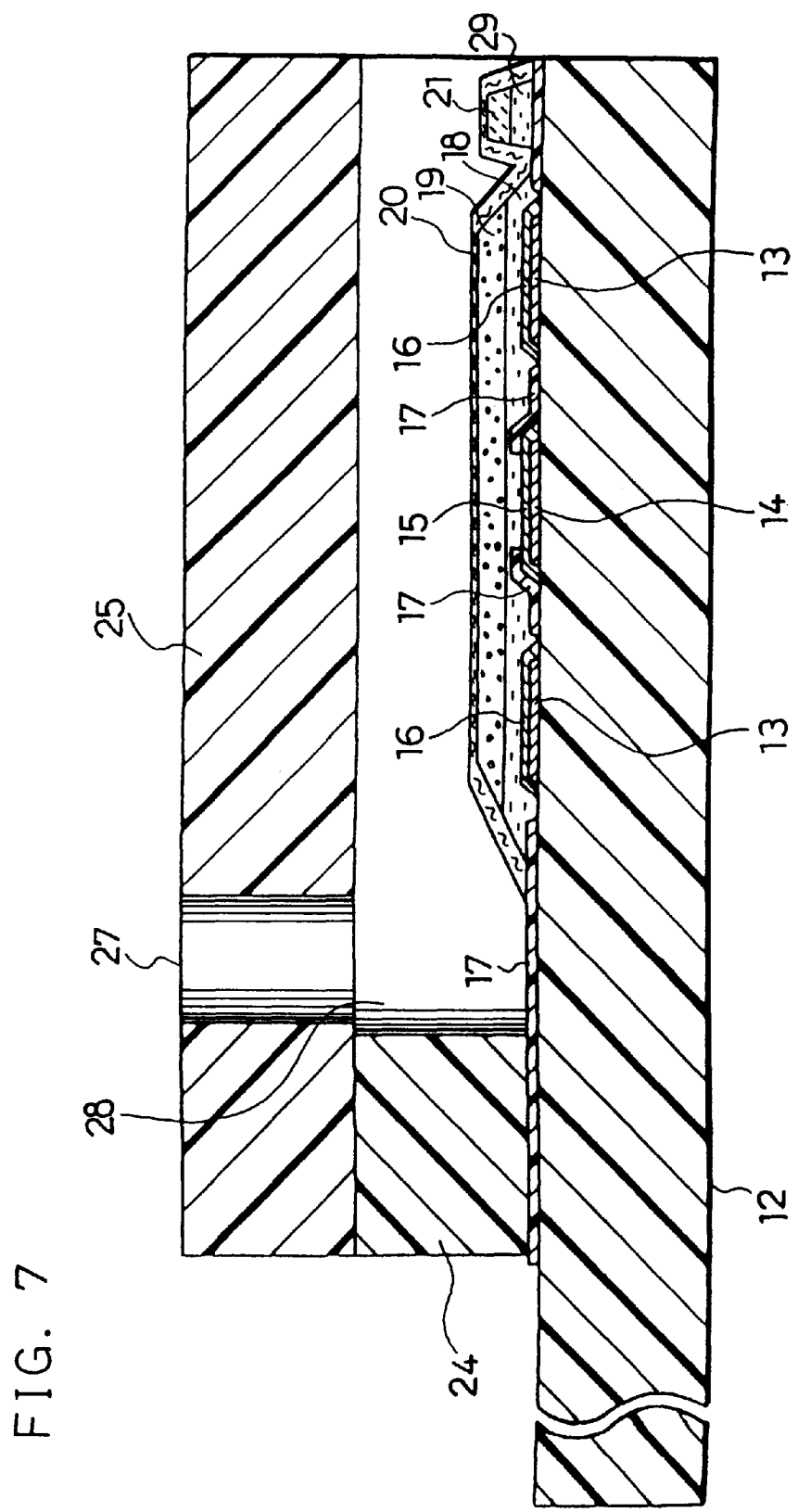
FIG. 7 is a longitudinal cross-sectional view showing the configuration of an essential part of the cholesterol sensor in still another embodiment of the present invention.

FIG. 7 is a longitudinal cross-sectional view of the cholesterol sensor of this example.

The CMC layer 18 is formed on the electrode system of the base plate in a manner similar to that of Example 2. On a position of the sample supplying channel 28 between the CMC layer 18 and the open inlet at the tip of the base plate which does not cover the part of the electrodes, another CMC layer 29 is formed so as not to contact the CMC layer 18 in the same manner as that applied for the CMC layer 18. The CMC layer 29 is not necessarily the same as the CMC layer 18.

Then, prepared is a mixed aqueous solution containing the ChDH derived from Nocardia species in 10 unit/ml, the NDA which is a co-enzyme in 50 mM/l, diaphorase, the enzyme derived from Pseudomonas species in 10 unit/ml, potassium ferricyanide which is an electron mediator in 50 mM/l, ChE derived from Pseudomonas species in 1 k unit/ml, n-octyl-β-D-thioglucoside which is the surfactant in 0.5 wt %, and Tris hydrochloride which is a buffer agent in 0.3 M/l and the mixture adjusted to pH 8.5.

By dropping this aqueous solution (5 μl) on the CMC layer 18 so as not to contact the CMC layer 29 and drying it in a dried air at room temperature for 30 minutes, a ChDH-ChE-potassium ferricyanide-surfactant-NAD-diaphorase-buffer agent layer 19 is formed.

By dropping 5 μl of a 50 mM solution of NQS so as to cover the CMC layer 29 and subsequent drying in air at room temperature, an NQS layer 21 is formed. Instead of the CMC layer 29 and the NQS layer 21, it is possible to provide a layer containing both CMC and NQS by dropping a CMC aqueous solution containing NQS. Since NQS is relatively unstable at high PH, it should not be dissolved in a solution containing a buffer agent such as Tris hydrochloride and stood still for a long period after dissolution. By separating NQS from the buffer agent as disclosed, it is possible to incorporate the NQS into a sensor as the electron mediator. In dropping the above-mentioned NQS solution on the CMC layer 29 for forming the NQS layer 21, a care should be taken not to cause the NQS solution to contact the ChDH-ChE-potassium ferricyanide-surfactant-NAD-diaphorase-buffer agent layer 19.

On both the ChDH-ChE-potassium ferricyanide-surfactant-NAD-diaphorase-buffer agent layer 19 and the NQS layer 21, a lecithin layer 20 is formed by dropping 5 μl of a 5 wt % toluene solution of phosphatidyl choline and subsequent drying. Although the presence of this lecithin layer helps smooth introduction of the sample solution, this lecithin layer is not indispensable for the enzyme reaction. The lecithin layer 20 may also be formed on surfaces of a recess defined by the covering member comprised of the spacer 24 and the cover 25, i.e., the surfaces which are exposed to the sample supplying channel.

After forming the reaction layer comprising the CMC layer 18, the CMC layer 29, the ChDH-ChE-potassium ferricyanide-surfactant-NAD-diaphorase-buffer agent layer 19, the NQS layer 21 and the lecithin layer 20, the cholesterol sensor is completed by adhering the cover 25 and a spacer 24 to the insulating base plate 12 in a positional relationship as indicated by the one dot-chain lines in FIG. 4.

EXAMPLE 5

Figure 8:
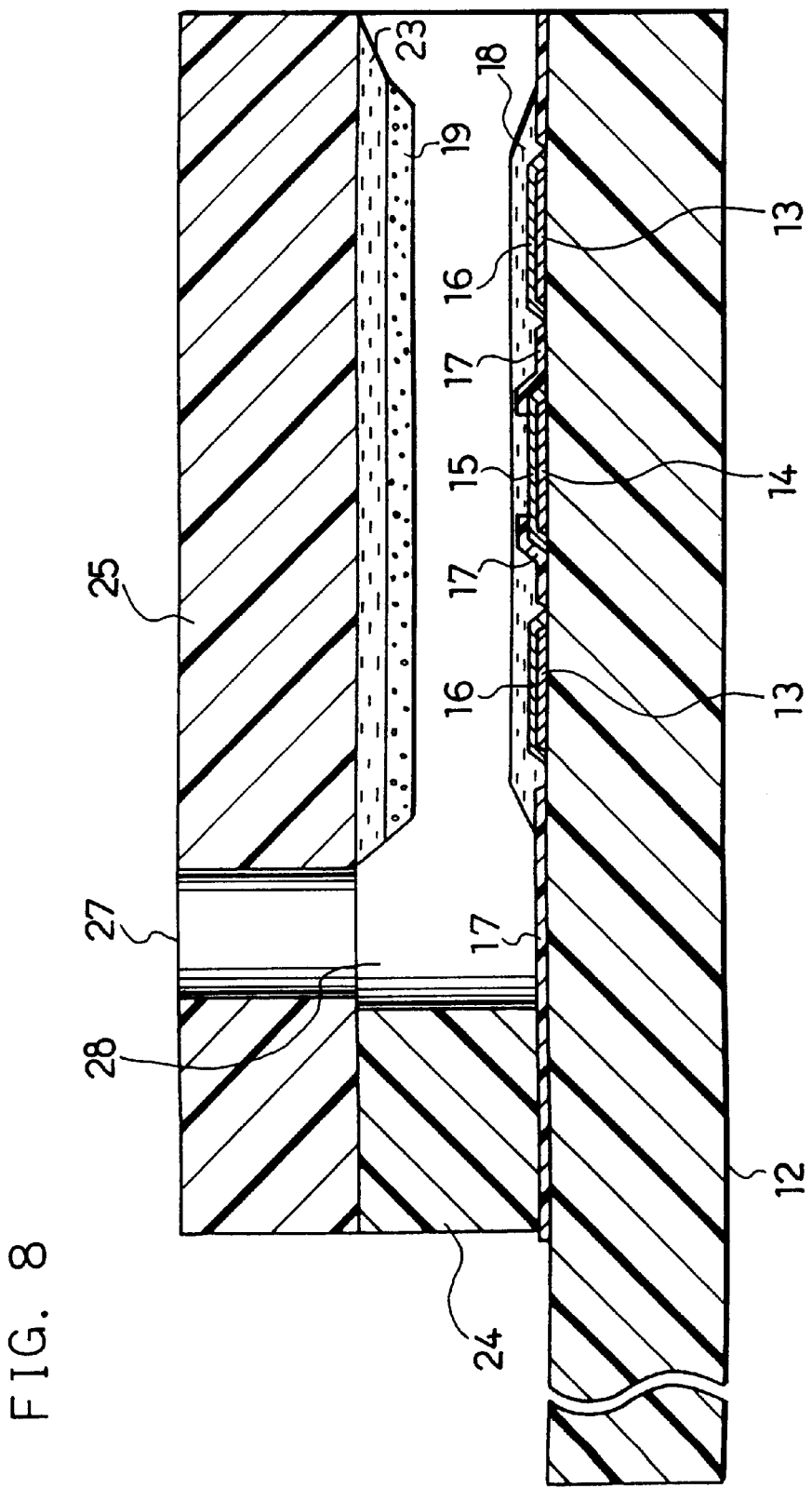
FIG. 8 is a longitudinal cross-sectional view showing the configuration of an essential part of the cholesterol sensor in still another embodiment of the present invention.

FIG. 8 is a longitudinal cross-sectional view of the cholesterol sensor of this example.

The CMC layer 18 is formed on the electrode system of the base plate by dropping a 0.5 wt % aqueous solution of CMC in a manner similar to that in Example 2.

Subsequently, another CMC layer 23 is formed on a recess part defined by the covering member comprising the spacer 24 and the cover 25 by dropping a 0.5 wt % aqueous solution of CMC in a manner similar to that in Example 3.

Then, prepared is a mixed aqueous solution containing the ChDH in 10 unit/ml, the NDA in 50 mM/l, diaphorase in 10 unit/ml, potassium ferricyanide which is an electron mediator in 50 mM/l, ChE derived from Pseudomonas species in 1 k unit/ml, n-octyl-β-D-thioglucoside which is the surfactant in 0.5 wt %, and Tris hydrochloride which is a buffer agent in 0.3 M/l, and the mixture is adjusted to pH 8.5.

By dropping 5 μl of this mixed aqueous solution over the CMC layer 23 so as to cover the CMC layer 23 and drying it in a dried air at room temperature for 30 minutes, a ChDH-ChE-potassium ferricyanide-surfactant-NAD-diaphorase-buffer agent layer 19 is formed.

By adhering the covering member comprised of the spacer 24 and the cover 25 provided with the reaction layer in the above-mentioned manner to the base plate 12, a cholesterol sensor is completed. This configuration of separating the reaction layer from the electrode system and forming only the CMC layer on the surface of the electrodes demonstrates a higher current value per unit substrate concentration than a configuration of providing the reaction layer on the surface of the electrodes.

The amounts of the respective reagents carried on the reaction layers shown in the forgoing examples are only exemplary and thus the present invention should not be limited to the shown amounts.

In order to facilitate introduction of the sample solution into the reaction reagent system, the cholesterol sensor in accordance with the present invention may provide a layer containing a lipid such as the lecithin layer 20 as shown in Example 2 over the surface of the reaction layer. In addition to the phosphatidyl choline employed in the foregoing examples, an amphipathic lipid such as phosphatidyl serine, phosphatidyl ethanol amine or another phospholipid may also be used as a lipid for this application.

In addition to the carboxymethyl cellulose (CMC) employed in the foregoing examples, polyvinyl pyrrolidone, polyvinyl alcohol, another water-soluble cellulose derivative such as ethyl cellulose and hydroxypropyl cellulose in particular, gelatin, polyacrylic acid and its salts, starch and its derivatives, maleic anhydride and its salts, polyacrylamide, methacrylate resin, poly-2-hydroxyethyl methacrylate and the like may also be used as the hydrophilc polymer for forming the reaction layer.

In the foregoing examples, Pseudomonas-derived ChE was employed as the ChE and n-octyl-β-D-thioglucoside as the surfactant, but a preferable response may also be obtained by using Lubrol PX (trade name), sodium cholate, dodecyl-β-D-maltoside, or DK-ester (trade name) if Pseudomonas-derived ChE is adopted. Further, mammalian pancreas-derived ChE may also be used as the ChE. In that case, a much preferable response can be obtained if a surfactant having a bile acid skeleton such as sodium cholate or the like is combined.

In the foregoing Examples 2–5, although the descriptions are limited to the two-electrode system comprised only of the measuring electrode and the counter electrode, a more accurate measurement can be obtained by employing a three-electrode system including a reference electrode further.

As described previously, according to the present invention, it is possible to produce a cholesterol sensor capable of measuring the cholesterol concentration in the sample solution in a short period without any influence of by oxygen.

It is understood that various other modifications will be apparent to and can be readily be made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A cholesterol sensor comprising an electrode system including a measuring electrode and a counter electrode, and a reaction reagent system, wherein said reaction reagent system contains at least cholesterol dehydrogenase, nicotinamide adenine dinucleotide and an oxidized electron mediator, which is at least one selected from the group consisting of a 1,2-naphthoquinone-4-sulfonate, 1-methoxy-5-methylphenazinium sulfate, Meldola's blue, thionine, and dimethyl benzoquinone.

2. A cholesterol sensor comprising an insulating base plate, an electrode system including a measuring electrode and a counter electrode, said electrode system provided on said insulating base plate, and a dry reaction layer provided on or near said electrode system, wherein said reaction layer contains at least cholesterol dehydrogenase, nicotinamide adenine dinucleotide and an oxidized electron mediator, which is at least one selected from the group consisting of a 1,2-naphthoquinone-4-sulfonate, 1-methoxy-5-methylphenazinium sulfate, Meldola's blue, thionine, and dimethyl benzoquinone.

3. The cholesterol sensor in accordance with claim 2, wherein said reaction reagent system contains diaphorase.

4. The cholesterol sensor in accordance with claim 2, wherein said reaction reagent system contains cholesterol esterase and a surfactant.

5. A cholesterol sensor comprising an insulating base plate, an electrode system including a measuring electrode and a counter electrode which are provided on said insulating base plate, a covering member having a groove which is placed on said insulating base plate for defining a sample supplying channel which is extended from an end of said base plate to said electrode system, and a reaction layer provided on said base plate or said covering member so as to be exposed to said sample supplying channel and including a reaction reagent system, said reaction reagent system being dry, wherein said reaction reagent system contains at least cholesterol dehydrogenase, nicotinamide adenine dinucleotide and an oxidized electron mediator, which is at least one selected from the group consisting of a 1,2-naphthoquinone-4-sulfonate, 1-methoxy-5-methylphenazinium sulfate, Meldola's blue, thionine, and dimethyl benzoquinone.

6. The cholesterol sensor in accordance with claim 5, wherein said reaction layer is divided so as to be provided on both of said electrode system and said covering member.

7. The cholesterol sensor in accordance with claim 5, wherein said reaction layer contains a layer including a hydrophilic polymer in at least part of said reaction layer.

8. The cholesterol sensor in accordance with claim 5, wherein said reaction layer contains a layer including a hydrophilic polymer and an electron mediator in a mixed state, in at least part of said reaction layer.

9. The cholesterol sensor in accordance with claim 5, wherein said measuring electrode comprises carbon.

* * * * *